United States Patent [19]
Broude et al.

[11] Patent Number: 5,675,409
[45] Date of Patent: Oct. 7, 1997

[54] PLATE HOLDER FOR A SURFACE INSPECTION SYSTEM

[75] Inventors: Sergey V. Broude, Newton Centre, Mass.; David Giroux, Somersworth, N.H.; Abdu Boudour, West Newton, Mass.; Eric Chase, Carlisle, Mass.; Carl Johnson, Tewksbury, Mass.; Pascal Miller, North Chelmsford, Mass.; Nicholas Allen, Bedford, Mass.; Jay Ormsby, Salem, Mass.

[73] Assignee: QC Optics, Inc., Burlington, Mass.

[21] Appl. No.: 500,260

[22] Filed: Jul. 10, 1995

[51] Int. Cl.⁶ ................................................. G01N 21/88
[52] U.S. Cl. ........................................ 356/237; 250/243
[58] Field of Search ................................. 356/237, 243

[56] References Cited

U.S. PATENT DOCUMENTS

| | | | |
|---|---|---|---|
| 4,776,693 | 10/1988 | Imamura et al. | 356/243 |
| 4,952,058 | 8/1990 | Noguchi et al. | 356/237 |

*Primary Examiner*—Richard A. Rosenberger
*Attorney, Agent, or Firm*—Iandiorio & Teska

[57] ABSTRACT

A plate holder for a plate surface inspection system, the plate holder including a plate holder body and a calibration plate integral with the plate holder body thereby eliminating the need to load a separate special calibration plate in the plate holder each time the surface inspection system needs to be calibrated.

12 Claims, 3 Drawing Sheets

PLATE HOLDER FOR A SURFACE INSPECTION SYSTEM

FIELD OF INVENTION

A plate holder for a surface inspection system such as those used to inspect photolithographic masks and such a plate holder having an integrated calibration plate for calibrating the inspection system.

BACKGROUND OF INVENTION

Photolithographic masks have a chrome pattern on a glass or quartz substrate and are used in the manufacture of thousands of semi-conductor wafers during a production run in a "stepper" printing machine. Therefore, it is critical that the surface of the mask be free of contaminating particles lest the images of the particles be repeated on every wafer causing defects. Accordingly, the masks are typically inspected using very precise inspection systems shown, for example, in U.S. Pat. Nos. 4,943,734; 4,794,264; 4,794,265; and 5,389,794 incorporated herein by reference. These systems can also be used to inspect other types of surfaces hereinafter generically referred to as "plates".

As a mechanical plate holder/spindle assembly spins and/or translates the plate, the surface of the plate is illuminated by a laser beam directed to the surface by means of a parabolic mirror and the scattering of the laser beam from the surface is analyzed: the scattering from the surface is different if a flaw or particle is present than if no particle or flaw is present. This scattering is also indicative of the size of a detected particle.

One prior method for calibrating such an inspection system is to load a special calibration plate onto the plate holder and execute a calibration routine. The calibration plate is a photolithographic mask with a particle or particles and/or defects of known sizes and positions intentionally placed on the surface of the mask. The calibration routine involves aiming the laser at the calibration plate and analyzing whether the inspection system accurately detects and classifies the known particles and defects.

The problem with this technique is that it is time consuming: the inspection of a production plate must be halted, the plate under inspection removed, the calibration plate loaded, the calibration routine completed, the calibration plate removed, and then the inspection run started again. This technique is also labor intensive. Worse, the operating parameters of the system can vary between the time the calibration plate is removed and the next production plate to be inspected is loaded. Also, the calibration plates themselves are expensive and require very special handling to prevent contamination by particles or defects. Finally, it is often difficult to assure that the calibration plate is referenced to the same position as a plate to be inspected. If the calibration plate does not lie in the same plane as a plate to be inspected, the calibration routine results in errors.

SUMMARY OF INVENTION I

It is therefore an object of this invention to provide a plate holder for a surface inspection system which facilitates self-calibration.

It is a further object of this invention to provide such a plate holder which does not require the use of a separate calibration plate and which eliminates the time consuming and labor intensive calibration operations inherent with the use of a separate calibration plate.

It is a further object of this invention to provide such a plate holder which facilitates calibration at any time, even with a production plate, such as a photolithographic mask to be inspected, in place in the holder.

It is a further object of this invention to provide such a plate holder which insures that the calibration plate is referenced to lie in the same plane as the plate to be inspected to prevent calibration errors.

This invention results from the realization that instead of using a separate calibration plate which must be installed, aligned, and then removed from the plate holder of a surface inspection system, if a calibration plate is made a part of the plate holder itself then the surface inspection system can be calibrated at any time—even with a production plate such as a photolithographic mask to be inspected in place in the plate holder. This invention results from the further realization that the calibration plate can be easily referenced to lie in the same plane as the plate to be inspected if the calibration plate is held in place by the same members which reference the production plates to be inspected. Since the calibration plate is integral with the plate holder, there may be two or even more calibration plates located on the plate holder for increased calibration accuracy and reliability.

This invention features and, depending on the specific implementation, may comprise, include, consist essentially of, or consist of a plate holder for a plate surface inspection system. The plate holder comprises a plate holder body and a calibration plate integral with the plate holder body to eliminate the need for a separate special calibration plate loaded into the plate holder each time the plate surface inspection system is calibrated.

The plate holder may further include a second calibration plate integral with the plate holder body. The calibration plate may include a protective pellicle. Further included are means for referencing the calibration plate to lie in the same plane as a plate to be inspected held by the plate holder. The plate holder body includes a top surface and a set of tabs positioned on the top surface extending transversely therefrom for referencing a plate to be inspected in a plane defined by the underside surfaces of the transversely extending tabs.

The means for referencing includes a cavity in the top surface underneath one of the tabs and the calibration plate is positioned in the cavity and referenced to the underside of that tab which further includes a window for viewing the calibration plate. The body may include a number of recesses for receiving robot fingers which position a plate to be inspected in the holder.

This invention also features a plate holder comprising a plate holder body including a machined top surface and a set of machined tabs positioned on the top surface extending transversely therefrom for referencing a plate to be inspected in a plane defined by the underside surfaces of the transversely extending tabs; and a calibration plate integral with the top surface of the plate holder body. Further included are means for referencing the calibration plate to one of the tabs for insuring the calibration plate and a plate to be inspected held by the plate holder lie in the same plane. The plate holder body includes a cavity in the top surface underneath at least one tab, the calibration plate is positioned in the cavity and referenced to the underside of that tab which includes a window for viewing the calibration plate.

DISCLOSURE OF PREFERRED EMBODIMENT

Other objects, features and advantages will occur to those skilled in the art from the following description of a preferred embodiment and the accompanying drawings, in which.

Figure 1:
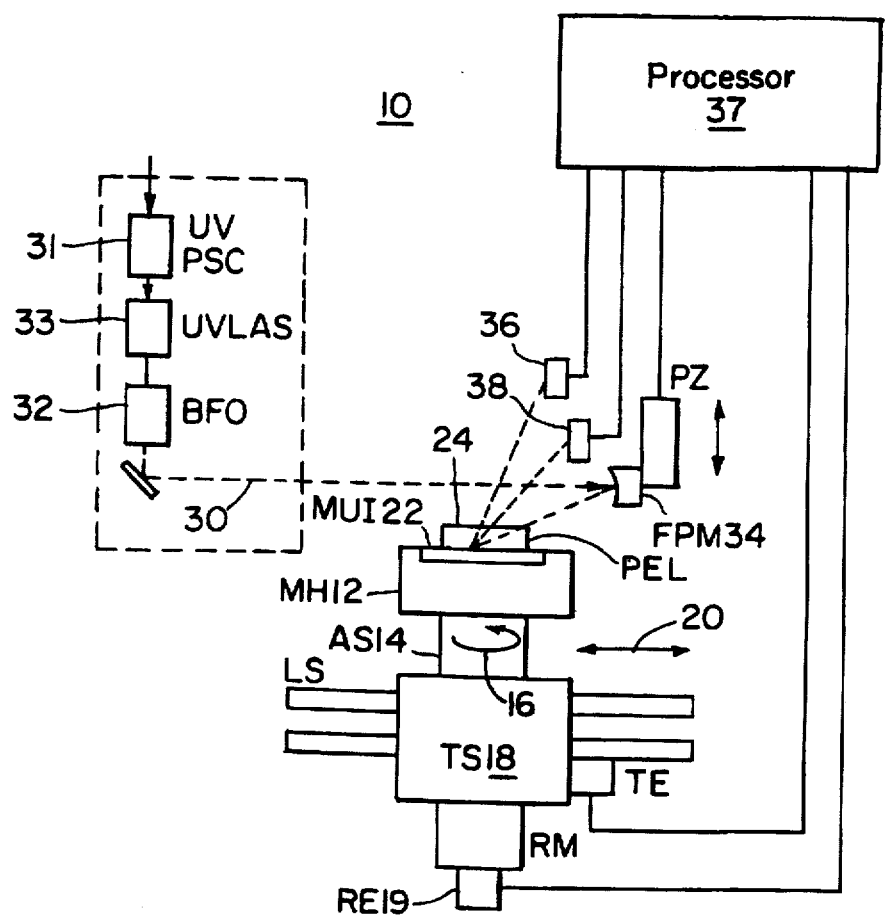
FIG. 1 is a block diagram of a surface inspection apparatus including the self-calibrating plate holder of this invention.

Plate inspection system 10, FIG. 1 includes plate holder assembly 12 mounted on spindle 14 which rotates in the direction shown by arrow 16 and which in turn is mounted on translation stage 18 which moves in the direction shown by arrow 20. A plate such as a photolithographic mask 22 having protective pellicle 24 is mounted on plate holder assembly 12 and inspected in the following manner. Laser beam 30 from beam forming optics 32 is directed via parabolic mirror 34 through pellicle 24 to surface 22. Scattering of the laser beam from the surface, as detected by sensors 36 and 38, is indicative of the presence and size of particle or flaw on surface 22. See, e.g. U.S. Pat. No. 4,943,734 and No. 5,389,794. Processor 37 analyzes the signals from detectors 37 and 38 and from translation stage 18 and rotary encoder 19 to calculate the position and size of any flaws on surface 22.

As explained in the Background of Invention above, in order to calibrate system 10, a special calibration plate with particles of a specific size intentionally placed thereon is loaded on holder 12. A calibration routine is completed to ensure system 10 is operating properly. The amplitude and pulse duration of the scattering of light by the artifact on the calibration plate is measured and compared with standard data. Corrective action can then be implemented by adjusting the power supply 31 of the laser 33 or the position of parabolic mirror 34.

Figure 2:
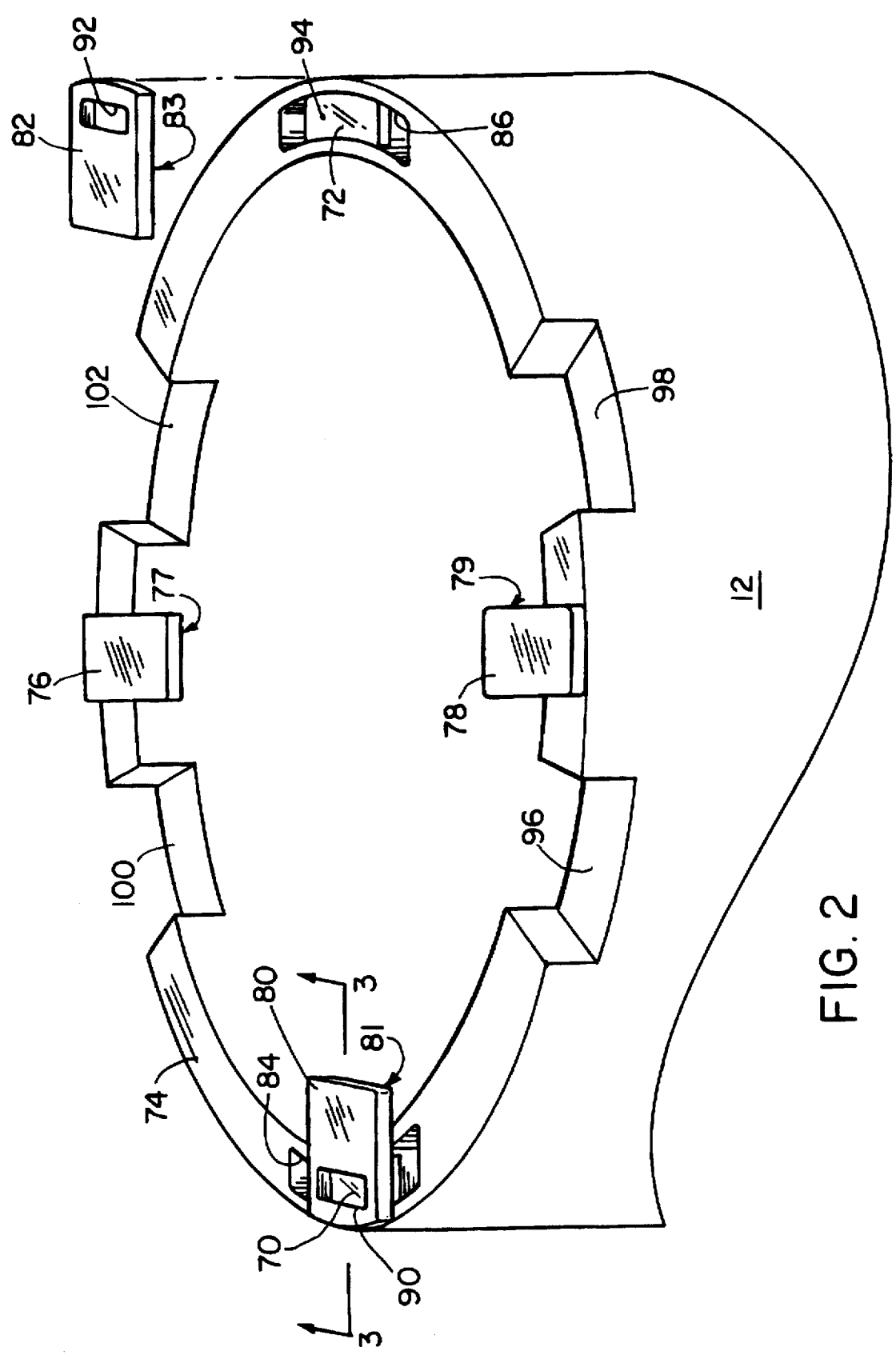
FIG. 2 is an enlarged, three-dimensional schematic partially exploded view of the self-calibrating plate holder of this invention.

In this invention, however, a separate calibration plate is not required. Plate holder assembly 12, FIG. 2, includes integral calibration plates 70 and 72 so that inspection device 10, FIG. 1, can be calibrated at any time even with a production plate to be inspected in place within plate holder assembly 12, FIG. 2. Calibration plate 72 provides a back-up for calibration plate 70 thereby providing increased calibration accuracy and reliability.

Top surface 74 of holder assembly 12 is precisely machined with a flatness better than 0.5 micron.

Transversely extending tabs 76, 78, 80 and 82 are also precisely machined on the bottom surface thereof so that when they are affixed to precisely machined top surface 74, the top surface of a plate to be inspected referenced up against the underside surfaces 77, 79, 81, and 83 of tabs 76, 78, 80 and 82 will lie flat in a reference plane defined by the tabs to insure that the laser beam is always focused properly on a plate held in place by plate holder assembly 12. The plate is referenced against the undersides of tabs 76, 78, 80 and 82 so that variations in the thickness of a given plate will not affect the inspection as the laser beam traces a spiral pattern over the surface of the plate.

Calibration plates 70 and 72 are fitted within cavities 84 and 86, respectively, within top surface 74 of plate holder assembly 12. These cavities are partially covered as shown by tabs 80 and 82. Tabs 80 and 82 each have a window 90 and 92 so that the laser beam can impinge upon known artifacts as shown at 94 on calibration plate 72.

Plate holder assembly 12 according to this invention also includes slots 96, 98, 100 and 102 to receive the fingers of a robot arm which automatically places a plate to be inspected in plate holder assembly 12.

Figure 3:
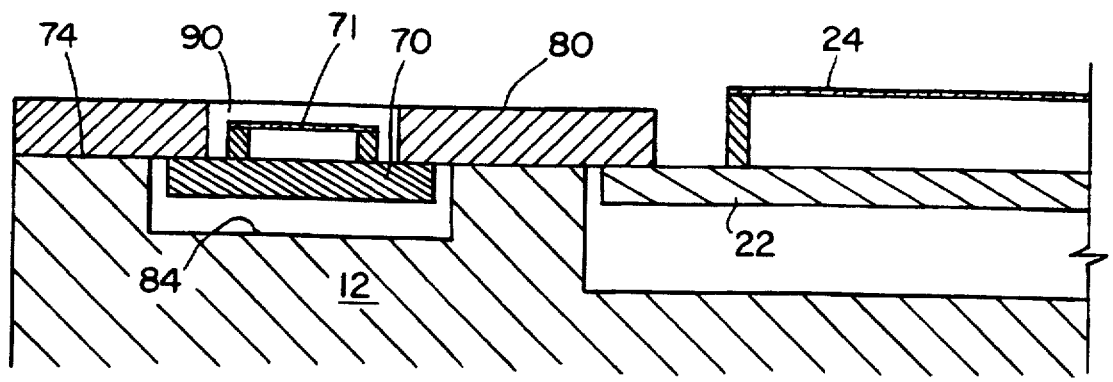
FIG. 3 is a cross-sectional view of a portion of the holder taken along line 3—3 of FIG. 2 including the integral calibration plate of this invention.

In order to insure that calibration plate 70, FIG. 3 for example, lies in the same plane as plate 22 to be inspected, both calibration plate 70 and the plate 22 to be inspected are referenced underneath the same tab 80 affixed to machined top surface 74. Calibration plate 70 with protective pellicle 71 is placed in cavity 84 formed in top surface 74 of plate holder assembly 12 and referenced upwards against tab 80 in the same way that a plate 22 to be inspected is referenced upwards against tab 80 thereby assuring that the top surface of the calibration plate is in the same plane as the top surface of the plate 22 to be inspected.

Figure 4:
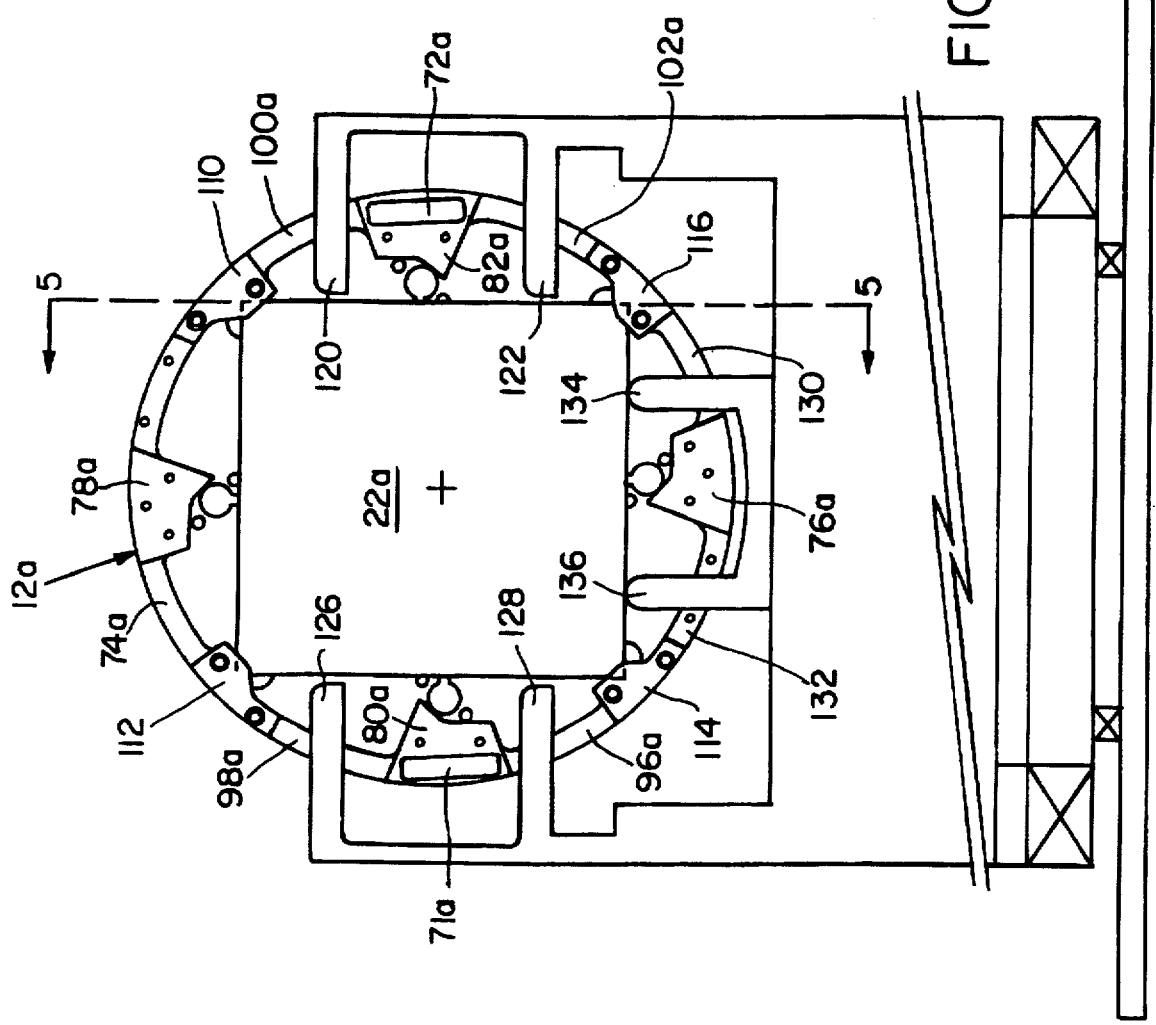
FIG. 4 is a top plan view of the plate holder assembly of this invention.

In a preferred embodiment, holder assembly 12a, FIG. 4 includes precisely machined tabs 80a and 82a covering and referencing calibration plates 71a and 72a. Tabs 80a and 82a are used in conjunction with tabs 76a and 78a for a 5"×5" photolithographic mask (not shown). Tabs 110, 112, 114 and 116 are used for referencing 6"×6" mask 22a.

Figure 5:
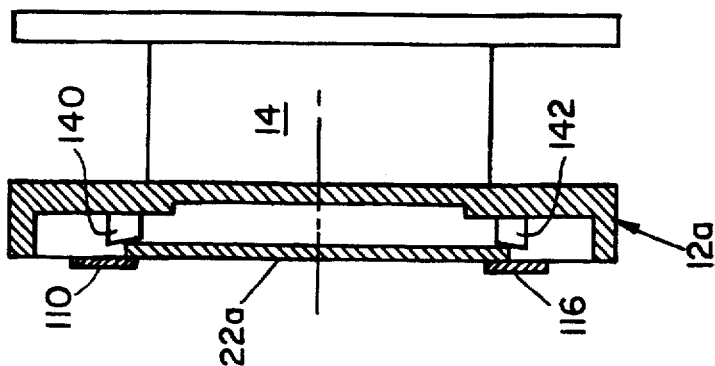
FIG. 5 is a cut away side view of the plate holder assembly taken along line 5—5 of FIG. 4.

Plate holder assembly 12a features recesses 96a, 98a, 100a and 102a, to receive robot fingers 128, 126, 120 and 128, respectively, as well as recesses 130 and 132 for robot fingers 134 and 136, respectively, used to position plate 22a in plate holder assembly 12a. As shown in FIG. 5, pins 140 and 142 press plate 22a against tabs 110 and 116. Pins 140 and 142 have angled top surfaces to also reference plate 22a in a direction along the plane of the plate as required when the plate holder is oriented to hold a plate in a vertical rather than a horizontal position. The vertical orientation is preferred to limit the mount of contamination of the plate to be inspected by airborne particles.

Calibration plates 71a and 72a are formed of a substrate equivalent to the substrate of the plate 22 to be inspected. Therefore, if the plate 22a to be inspected is a photolithographic mask having a chrome pattern on a glass substrate, then calibration plates 71a and 72a also include a chrome pattern on a glass substrate. A particle or artifact such as a pit or mound is deposited on the surface of calibration plate 71a and/or plate 72a. The deposited particle or artifact should exhibit a laser beam scatter pattern equivalent to the types of particles expected to be found on production plate 22a. Calibration plates 71a and 72a are preferably protected with their own pellicles to prevent any contamination. One, two, or even more calibration plates may be used depending on the specific implementation.

Although specific features of the invention are shown in some drawings and not others, this is for convenience only as some feature may be combined with any or all of the other features in accordance with the invention. Other configuration of plate holders are possible and can be modified to include integral calibration plates in accordance with this invention thus eliminating the need for separate calibration plates. Other means for assuring that the calibration plates lie in the same plane as the surface to be inspected are also possible. Therefore, other embodiments will occur to those skilled in the art and are within the following claims:

What is claimed is:

1. A plate holder comprising:
   a plate holder body including a machined top surface and a set of machined tabs positioned on said top surface extending transversely therefrom for referencing a plate to be inspected in a plane defined by the underside surfaces of said transversely extending tabs; and a calibration plate integral with the top surface of said plate holder body.

2. The plate holder of claim 1 further including means for referencing said calibration plate to one of said tabs for insuring said calibration plate and a plate to be inspected held by said plate holder lie in the same plane.

3. The plate holder of claim 2 further including a cavity in said top surface underneath at least one tab, said calibration plate positioned in said cavity and referenced to the underside of said one tab.

4. The plate holder of claim 3 in which said one tab includes a window for viewing said calibration plate.

5. The plate holder of claim 2 further including a cavity in said top surface underneath at least one tab, said calibration plate positioned in said cavity and referenced to the underside of said one tab.

6. A plate holder comprising:

a plate holder body including a machined top surface and a set of machined tabs positioned on said top surface extending transversely therefrom for referencing a plate to be inspected in a plane defined by the underside surfaces of said transversely extending tabs; and a calibration plate integral with said plate holder body.

7. A plate holder for a plate surface inspection system, the plate holder comprising:

a plate holder body including a top surface and a set of tabs positioned on said top surface extending transversely therefrom and means for referencing a plate to be inspected against the underside surfaces of said transversely extending tabs; and a calibration plate integral with said plate holder body.

8. The plate holder of claim 7 in which said means for referencing a plate to be inspected include a set of members, one for each said tab, for urging the plate to be inspected against the underside surfaces of said tabs.

9. The plate holder of claim 7 further including a cavity in said top surface underneath one said tab, said calibration plate positioned in said cavity and referenced to the underside of said tab.

10. The plate holder of claim 9 in which said one tab further includes a window for viewing said calibration plate.

11. The plate holder of claim 7 in which said body further includes a number of recesses for receiving robot fingers which position a plate to be inspected in said holder.

12. A plate holder comprising:

a plate holder body including a machined top surface and a set of machined tabs positioned on said top surface extending transversely therefrom for referencing a plate to be inspected in a plane defined by the underside surfaces of said transversely extending tabs;

a cavity in said top surface underneath at least one tab; and a calibration plate integral with the top surface of said plate holder body and residing in said cavity.

* * * * *